United States Patent
Tol et al.

(10) Patent No.: US 9,278,225 B2
(45) Date of Patent: Mar. 8, 2016

(54) APPARATUS WITH INTERNAL POWER TRANSFER

(75) Inventors: Jeroen Jacob Arnold Tol, Eindhoven (NL); Franciscus Paulus Maria Budzelaar, Eindhoven (NL)

(73) Assignee: Koninklijke Philips Electronics, Eindhoven (NL)

( * ) Notice: Subject to any disclaimer, the term of this patent is extended or adjusted under 35 U.S.C. 154(b) by 638 days.

(21) Appl. No.: 13/383,601

(22) PCT Filed: Jun. 30, 2010

(86) PCT No.: PCT/IB2010/052987
§ 371 (c)(1),
(2), (4) Date: Jan. 12, 2012

(87) PCT Pub. No.: WO2011/007281
PCT Pub. Date: Jan. 20, 2011

(65) Prior Publication Data
US 2012/0120684 A1    May 17, 2012

(30) Foreign Application Priority Data
Jul. 15, 2009   (EP) .................................... 09165520

(51) Int. Cl.
| H02M 3/335 | (2006.01) |
| A61N 1/378 | (2006.01) |
| A61N 1/08 | (2006.01) |
| A61N 1/05 | (2006.01) |
| H02M 3/28 | (2006.01) |
| H02J 7/00 | (2006.01) |
| H02J 1/00 | (2006.01) |
| H02M 7/48 | (2007.01) |

(52) U.S. Cl.
CPC  *A61N 1/378* (2013.01); *A61N 1/08* (2013.01); *H02J 7/0065* (2013.01); *H02J 2001/002* (2013.01); *H02M 7/48* (2013.01)

(58) Field of Classification Search
CPC  ... H02M 3/335; H02M 7/521; H02M 3/3376; H02M 3/33569; H02M 3/3374; H02M 3/28
USPC  ............ 607/2, 33, 61, 72, 115, 116; 323/911; 363/15, 16, 17
See application file for complete search history.

(56) References Cited

U.S. PATENT DOCUMENTS

| 3,888,260 | A |   | 6/1975 | Fischell |
| 4,431,001 | A |   | 2/1984 | Hakansson et al. |
| 4,516,820 | A |   | 5/1985 | Kuzma |
| 4,523,269 | A | * | 6/1985 | Baker et al. .................. 363/138 |

(Continued)

FOREIGN PATENT DOCUMENTS

EP        1424098        2/2004

OTHER PUBLICATIONS

Powell, William B. And Pheifer, David. The Electrolytic Tilt Sensor. Sensors Magazine. May 2000. Questex Media Group, Inc.

(Continued)

*Primary Examiner* — Gary L Laxton (57) ABSTRACT

An electronic apparatus with a DC power source and power-consuming electronic circuits and a method of transferring power between these components include converting the DC voltage of the power source into an AC voltage which is then transferred via a connector to the electronic circuits.

21 Claims, 4 Drawing Sheets

(56) References Cited

U.S. PATENT DOCUMENTS

| | | | |
|---|---|---|---|
| 5,027,264 A * | 6/1991 | DeDoncker | H02M 3/33584 363/129 |
| 5,115,386 A * | 5/1992 | Shirahama et al. | 363/41 |
| 5,134,307 A * | 7/1992 | Nakano | 307/87 |
| 5,948,006 A | 9/1999 | Mann | |
| 6,308,101 B1 | 10/2001 | Faltys et al. | |
| 6,507,503 B2 * | 1/2003 | Norrga | 363/17 |
| 6,678,559 B1 * | 1/2004 | Breyen et al. | 607/5 |
| 7,199,535 B2 * | 4/2007 | Welchko | B60L 11/12 307/65 |
| 7,211,351 B2 | 5/2007 | Klaassen | |
| 7,337,010 B2 | 2/2008 | Howard et al. | |
| 7,496,404 B2 | 2/2009 | Meadows et al. | |
| 8,295,941 B2 * | 10/2012 | Hyde et al. | 607/61 |
| 2008/0186742 A1 * | 8/2008 | Seong | H02M 3/3376 363/17 |
| 2008/0186751 A1 * | 8/2008 | Tokuyama et al. | 363/131 |

OTHER PUBLICATIONS

Mihaiu, M.I., Toward the "Ideal Diode" Using Power Mosfet in Full Wave Synchronous Rectifiers for Low Voltage Power Supplies. 2008 International Symposium on Power Electronics, Electrical Drives, Automation and Motion., University of Craiova, Romania.

Powell, W.B. et al: "The Electrolytic Tilt Sensor", May 1, 2000, XP055180998.

EPO Form 2906 01.91 TRI dated Apr. 14, 2015, application No. 10752394.6.

* cited by examiner

APPARATUS WITH INTERNAL POWER TRANSFER

FIELD OF THE INVENTION

The invention relates to an electronic apparatus, for example a product of consumer electronics or a medical implant, that comprises a DC power source from which electrical power has to be transferred to power-consuming electronic circuits.

The invention further relates to a method for transferring electrical power inside such an electronic apparatus.

The invention further relates to a supply module for use in such an electronic apparatus, for transferring power to the power consuming electronics circuits.

BACKGROUND OF THE INVENTION

A medical implant like a pacemaker or a Deep Brain Stimulation system is a typical example of an electronic apparatus in which electrical power has to be transferred from a DC power storage (battery) to power-consuming circuits. Due to its operation in a wet environment, care must be taken to avoid harmful effects like electrolysis when electronic components of an implant come into contact with moisture. In the U.S. Pat. No. 3,888,260, this is achieved by providing an implant with a double hermetic sealing. However, when the battery of an implant shall be replaced at the end of its lifetime, it is difficult to do this without permanently damaging such a sealing.

SUMMARY OF THE INVENTION

Based on this background, it was an object of the present invention to provide means that allow a safe energy transfer between a DC power source and electronic circuits even in problematic environments, for example when being exposed to moisture.

An electronic apparatus according to the present invention comprises the following components:

a) A "supply module" which comprises a DC (direct current) power source and (typically at least two) power output terminals, i.e. electrical contacts via which the DC power source can supply electrical energy to a consumer.

b) A "consumer module" which comprises (typically at least two) power input terminals (via which the consumer module can receive electrical energy) and power-consuming electronic circuits. The nature and design of the electronic circuits can vary largely depending on the purpose the electronic apparatus is intended for.

c) A connector via which corresponding power output terminals and power input terminals can reversibly be electrically connected. The connector will for example have a plug-and-socket like design with corresponding male and female contacts as it is known in the state of the art. However, it should be noted that the realization of the terminals and the connector may largely vary as long as the desired energy transfer is achieved. Hence a terminal may also be realized by a casing of the apparatus, or the connector may comprise a merely capacitive coupling between the power output and power input terminals.

d) A DC-AC converter (also called "DC inverter") that is arranged in the supply module between the DC power source and the power output terminals. The DC-AC converter receives the DC voltage of the power source as an input, converts this into an AC (alternating current) output voltage, and supplies this AC voltage to the power output terminals.

The invention, in a further aspect, provide a corresponding method for transferring electrical power from a supply module with a DC power source and power output terminals to a consumer module with power input terminals and power-consuming electronic circuits via a connector for connecting corresponding power output terminals and power input terminals, said method comprising the following steps:

a) The conversion of the DC voltage provided by the DC power source into an AC voltage with the help of a DC-AC converter.

b) The provision of said AC voltage to the power output terminals.

The invention, in a further aspect, provides for a supply module for use in an apparatus according to the invention comprising:

a) a DC power source;
b) power output terminals; and
c) a DC-AC converter that is arranged between the DC power source and the power output terminals.

The described supply module in the electronic apparatus and the method convert the DC voltage that is supplied by an available DC power source into an AC voltage, which is then transferred via a connector to the consumer module. The use of a connector has the advantage that the supply module and the consumer module can readily be separated from each other, for example if an exhausted supply module shall be replaced by a fresh one. At the same time, detrimental effects of electrically conductive moisture that may enter the connector in a wet environment are minimized by having only an AC (and not a DC) voltage at the connector terminals.

In the following, various preferred embodiments of the invention will be described that relate to both the electronic apparatus and the method described above.

The DC power source in the supply module can be any kind of device that is able to provide a DC voltage and/or current. It could for example comprise means that harvest DC power from the environment (e.g. via body heat) and provide this to the consumer module, where the energy is consumed and/or stored (e.g. in a battery). In most cases, the DC power source will comprise an energy storage from which electrical power is taken. This storage may for example be a (high-capacity) capacitor. Most preferably, the storage is a battery in which electrical energy is electrochemically stored, wherein both rechargeable as well as disposable batteries may be used.

The parts of the supply module besides the power output terminals and/or the parts of the consumer module besides the power input terminals are preferably sealed, i.e. arranged in an encapsulation which prevents the entrance of moisture and/or dust from the outside. This makes the modules apt for an application in a wet environment.

In another preferred embodiment of the invention, a capacitor (called "blocking capacitor") is arranged between the DC-AC converter and a corresponding power output terminal. The blocking capacitor prevents that a DC voltage can appear between two power output terminals, thus making the supply module safe even in case of a failure in its electronic circuits because a DC voltage can never appear, and therefore no harmful effects like electrolysis can occur at the terminals.

The frequency of the AC output voltage that is provided by the DC-AC converter to the power output terminals preferably ranges between 1 Hz and 1 MHz. A suitable value can be chosen as the frequency which minimizes detrimental effects (e.g. electrolysis) in the particular environment in which the electronic apparatus shall be used.

According to a further development of the invention, the DC-AC converter can assume a "pulsed operation mode" with a pulsed activity. In this operation mode, the DC-AC converter alters phases in which it converts DC voltage to AC voltage and supplies the latter to the power output terminals with phases in which it does not convert DC voltage (the power output terminals are preferably grounded during these phases). It should be noted that the pulsed operation is an alternation that takes place on a higher level (with a lower frequency) than the AC voltage change during the phases of activity. The proposed pulsed operation of the DC-AC converter has the advantage that the critical periods of power transfer are concentrated to the phases of activity, leaving less time for the occurrence of negative effects such as leakage current.

According to a further development of the aforementioned embodiment, the phases of activity of the DC-AC converter in the pulsed operation mode are long enough to charge an intermediate power storage (e.g. a capacitor) in the consumer module substantially (i.e. to more than about 80%, preferably more than 90% of its capacity). The electronic circuits in the consumer module can then continuously be supplied with electrical power from the intermediate power storage, while it is not necessary that there is a continuous power transfer on the critical route via the connector.

Depending on their particular design, the power-consuming electronic circuits of the consumer module will typically require either AC power or DC power for their operation. In the first case, the AC voltage that is supplied by the DC-AC converter may either directly be used by the electronic circuits in the consumer module or after an additional (AC) conversion. In a preferred embodiment of the invention, the power-consuming electronic circuits in the consumer module require a DC voltage, and the apparatus additionally comprises an AC-DC converter that is arranged between the power input terminals and the power-consuming electronic circuits of the consumer module. In this case the conversion from DC to AC is done only as an intermediate step to provide a safe power transfer via the connector.

According to a further development of the aforementioned design, the apparatus comprises a capacitor (called "hold capacitor") that connects the outputs of the AC-DC converter. The hold capacitor can smooth out residual AC components and bridge switching times in the output of the AC-DC converter. Moreover, the hold capacitor can operate as an intermediate power storage like the one that was mentioned above in connection with a pulsed operation mode of the power transfer.

The DC-AC converter of the supply module may optionally be designed such that it substantially provides a square-wave output voltage. In this case the AC output voltage can readily be converted into a DC voltage again as it is only necessary to switch polarity at the transitions of the square-wave voltage.

Though the use of an AC voltage helps to minimize negative effects of a possible contamination of the connector with moisture, further measures could be taken to avoid such a contamination at all. Hence it is preferred that the connector comprises hydrophobic materials that repel moisture. Additionally or alternatively, the connector should comprise substantially no voids when it is in its connected state, wherein "substantially" means that the remaining voids are practically unavoidable due to manufacturing tolerances, material variations etc. Minimizing voids directly limits the volume that can be filled by possibly harmful moisture. Moreover, the connector may optionally be provided with redundant contacts to assure a safe operation even if some contacts should fail.

According to a preferred embodiment of the invention, the electronic apparatus is an implantable medical device, for example a cardiac pacemaker or a Deep Brain Stimulation (DBS) system, a surgical tool, or an ingestible electronic product (referred to as "e-medicines" or "e-pill"). These electronic devices are exposed to a wet and electrochemically active environment that may come into contact with electronic components of the apparatus. At the same time, safety requirements are of course extraordinarily high in these cases, as any malfunction may directly threaten the health of a patient. The present invention provides a favorable solution to this dilemma which guarantees a safe power supply and simultaneously allows an easy exchange of a battery if necessary.

According to another embodiment, the electronic apparatus of the invention may be a product of consumer electronics, particularly a media player or recorder (e.g. CD player, MP3 player, video apparatus, digital or analog camera), a cell phone, a calculator, a measuring device (e.g. an outdoor distance or temperature measuring device), a tool (a driller or a screw driver), equipment for pipelines (e.g. for flow measurements), a shaver, equipment used by divers or the like.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which.

Like reference numbers in the Figures refer to identical or similar components.

DESCRIPTION OF PREFERRED EMBODIMENTS

In the following, the invention will be described with respect to medical implants, though it is not restricted to this application.

It is difficult to come up with a mechanical design of a hermetically sealed implant that completely resists moisture and can still be reopened if a part needs to be replaced or repaired. Such a replacement is particularly necessary once in a while for a rechargeable battery in an implant at the end of its lifetime. For an easy replacement, a connector between battery and electronics of the implant (both hermetically sealed) may be provided. However, it is almost unavoidable in practice that moisture will enter between the contacts when the battery is surgically replaced or the device is implanted in the body. Therefore, electrolysis due to the DC battery voltage, which can lead to both the dissolution of the connector terminals as well as to the formation of gases, cannot be prevented when there is a DC voltage across the connector. Both effects can be dangerous and lead to an unreliable or even broken connection between battery and electronics and direct (e.g. via gases) or indirect (implant malfunction) injuries to the patient.

It would be much easier if moisture is allowed to enter the box containing battery and electronics and if the mechanical design resembles a (simple) connector between battery and electronics. To achieve this, the invention proposes to include a DC-AC converter in the replaceable battery. If the frequency of the alternating voltage of the DC-AC converter is sufficiently high, between tens of Hz and a few kHz, depending on the applied material of the contacts and the properties of the saline moisture creeping between the contacts, electrolysis is prevented (cf. D. Pheifer, W. B. Powell: "Introduction The Electrolytic Tilt Sensor", available from the internet at http://archives.sensorsmag.com/articles/0500/120/index.htm).

Hence the invention solves the problem of electrolysis and the formation of gases at the contacts of a connector between a replaceable battery and electronics powered by the battery when the connector is applied in a wet environment, for example in an implant, in which moisture can creep between the terminals of the connector. Optionally, the DC-AC converter can be put on the same chip that is usually included with (rechargeable) batteries to prevent deep discharge, monitor short circuit currents etc.

In the following, various realizations of the above concept will be described for an implant in which it is assumed that the electronics requires a DC voltage. To this end, an AC-DC converter (rectifier) will be added to the electronics of the implant. Furthermore, the following aspects should be taken into account:

The power transfer chain should have a high efficiency, and the needed electronics should have a small volume (implant!) and be reliable and safe even when moisture enters the connector between battery and implant electronics.

Leakage current through the saline moisture lowers the efficiency of the power transfer. This effect can be minimized by proper mechanical design (hydrophobic materials, non-conducting bio-compatible fillers and allowing moisture in narrow short cuts only) and duty-cycling the power transfer (i.e. pulsed power transfer).

The conversion from DC to AC can most simply be implemented by chopping the DC battery voltage with a full-bridge power stage and application of a (synchronous) full-wave rectifier to convert it back to DC.

Safety is improved by the insertion of a blocking capacitor in the power transfer path, because it prevents that a DC voltage appears across the connector, for example when the DC-AC converter fails. Redundant contacts help to improve the connector's reliability.

The largest component in the power transfer chain is the blocking capacitor and to a lesser extend the hold capacitor in the rectifier. A higher pulsed power transfer frequency leads to a reduction of their size.

Figure 1:
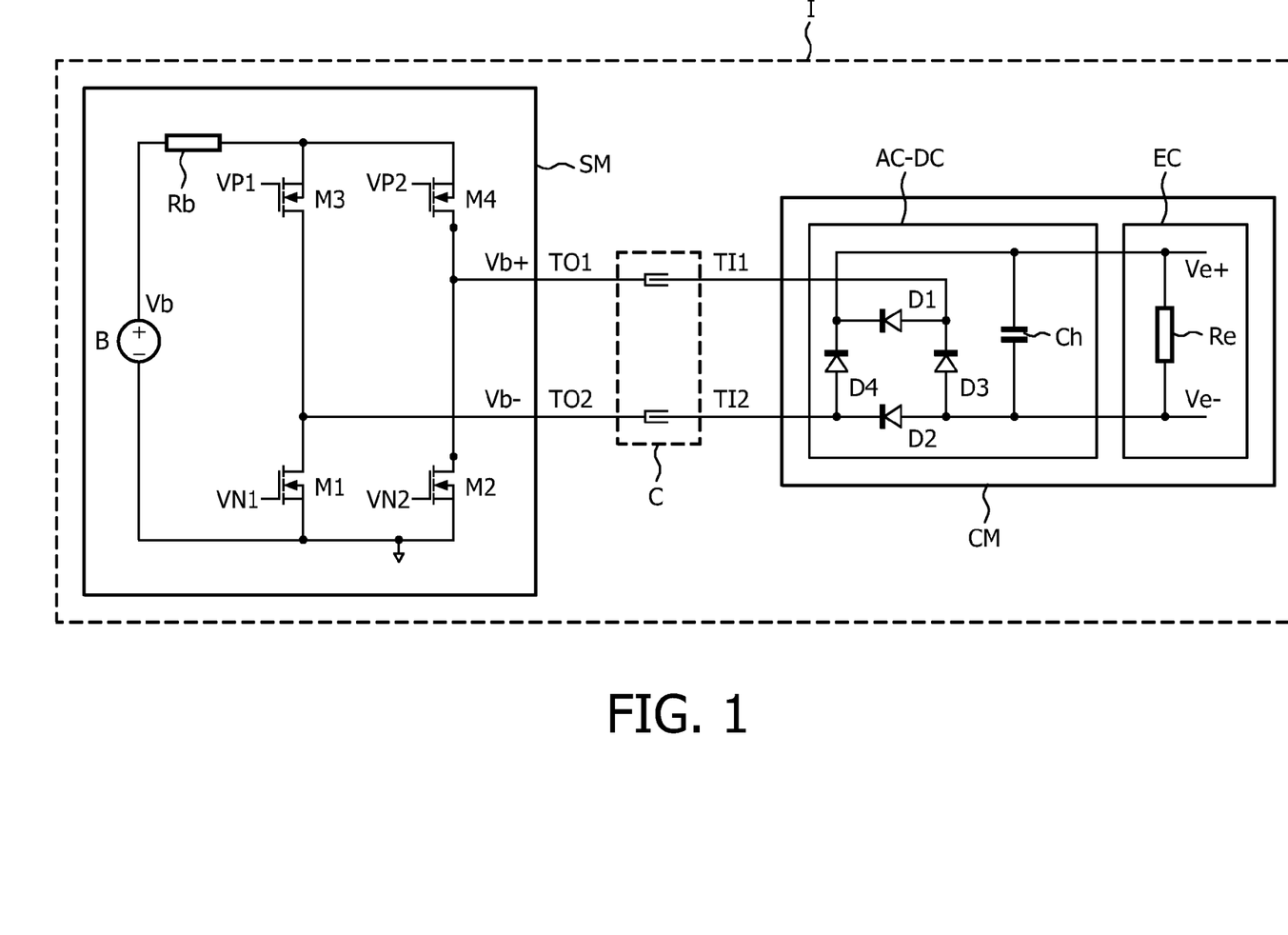
FIG. 1 shows a circuit diagram of an electronic apparatus according to the present invention.

FIG. 1 schematically illustrates an electronic apparatus I, for example an implant like a Deep Brain Stimulation (DBS) system, according to the present invention. The implant I comprises a "supply module" SM with a battery B providing a DC voltage Vb via a (small) internal (battery) resistance Rb, wherein the supply module is hermetically sealed with respect to the environment. The battery B may a replaceable battery. According to the invention, the DC voltage of the battery B is converted into an AC voltage by a full-bridge power stage comprising four transistors M1-M4. The resulting AC voltage is provided to two power output terminals TO1 and TO2 of the supply module SM. The output terminals alternate with opposite polarity Vb+ and Vb− between approximately ground and the battery voltage Vb.

The supply module is arranged such that it can be used in an electronic apparatus and that it can be replaced as a complete module if it this becomes necessary. This may happen typically when the included battery B is running towards its end of life. The supply module can be regarded as a standalone component with respect to the electronic apparatus. The supply module is hermetically sealed to withstand the environment inside the electronic apparatus in which the supply module will be placed. The supply module may optionally be equipped with a first "connector component" (e.g. a socket or a plug) adapted to form with a compatible second "connector component" a connector for reversibly connecting the power output terminals to corresponding terminals. This second "connector component" is then provided inside the electronic apparatus such that the supply module can be put into electronic apparatus and that the first connector component and the second connector component form a connection through which power is supplied to the circuits of the electronic apparatus.

The transistors M1-M4 are controlled by a generator G (not shown in FIG. 1). The generator G is separately shown in FIG. 4 together with exemplary control voltages VP1, VN1, VP2, VN2 for the transistors. In FIG. 1, the transistors M1 and M2 are NMOS transistors which conduct when their gate potential VN1 or VN2, respectively, is "high" (i.e. larger than their threshold voltage; usually the gates switch between 0 and the battery voltage Vb). The transistors M3 and M4 are PMOST transistors which conduct when their gate potential VP1 and VP2, respectively, is "low" (i.e. usually connected to ground). The transistors could for example be driven with the following sequence of "high" (H) and "low" (L) voltages: (VP1, VN1;VP2,VN2)=(H,H;L,L), (L,L;H,H) etc.

Figure 4:
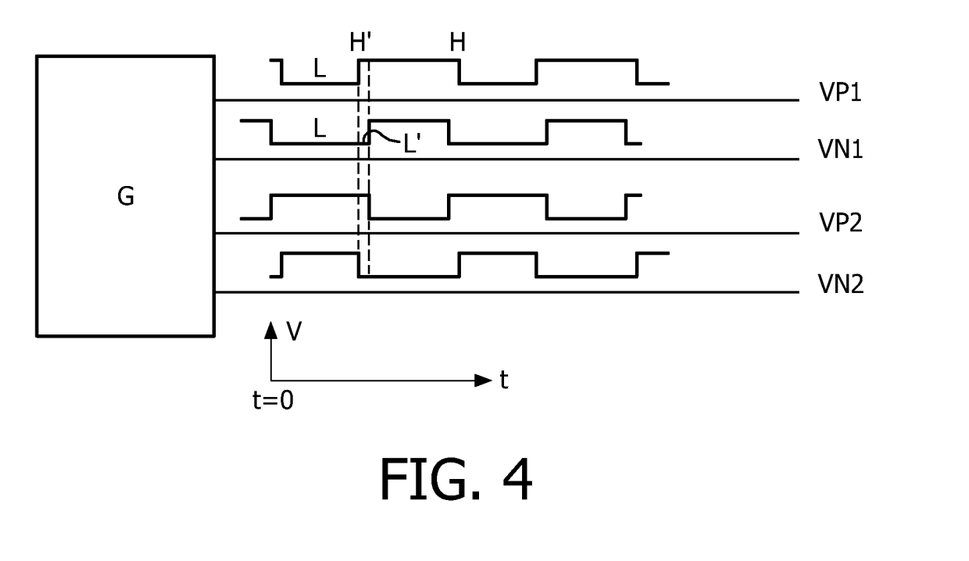
FIG. 4 illustrates possible control signals provided to the transistors in the DC-AC converter of FIG. 1.

In FIG. 4, another sequence is shown in which the control voltages are generated with non-overlapping clocks to prevent short-circuit currents in the full-bridge power stage. In this case there are short periods when all transistors are not conducting. The corresponding sequence of voltages is (with H', L' denoting a "high" and "low" voltage level when all transistors are not conducting): (VP1,VN1;VP2,VN2)=(H,H;L,L), (H',L';H',L'), (L,L,H,H), (H',L',H',L')

The implant I further comprises a connector C in which the output terminals TO1, TO2 of the supply module SM reversibly contact power input terminals TI1, TI2, respectively, of a "consumer module" CM.

Figure 2:
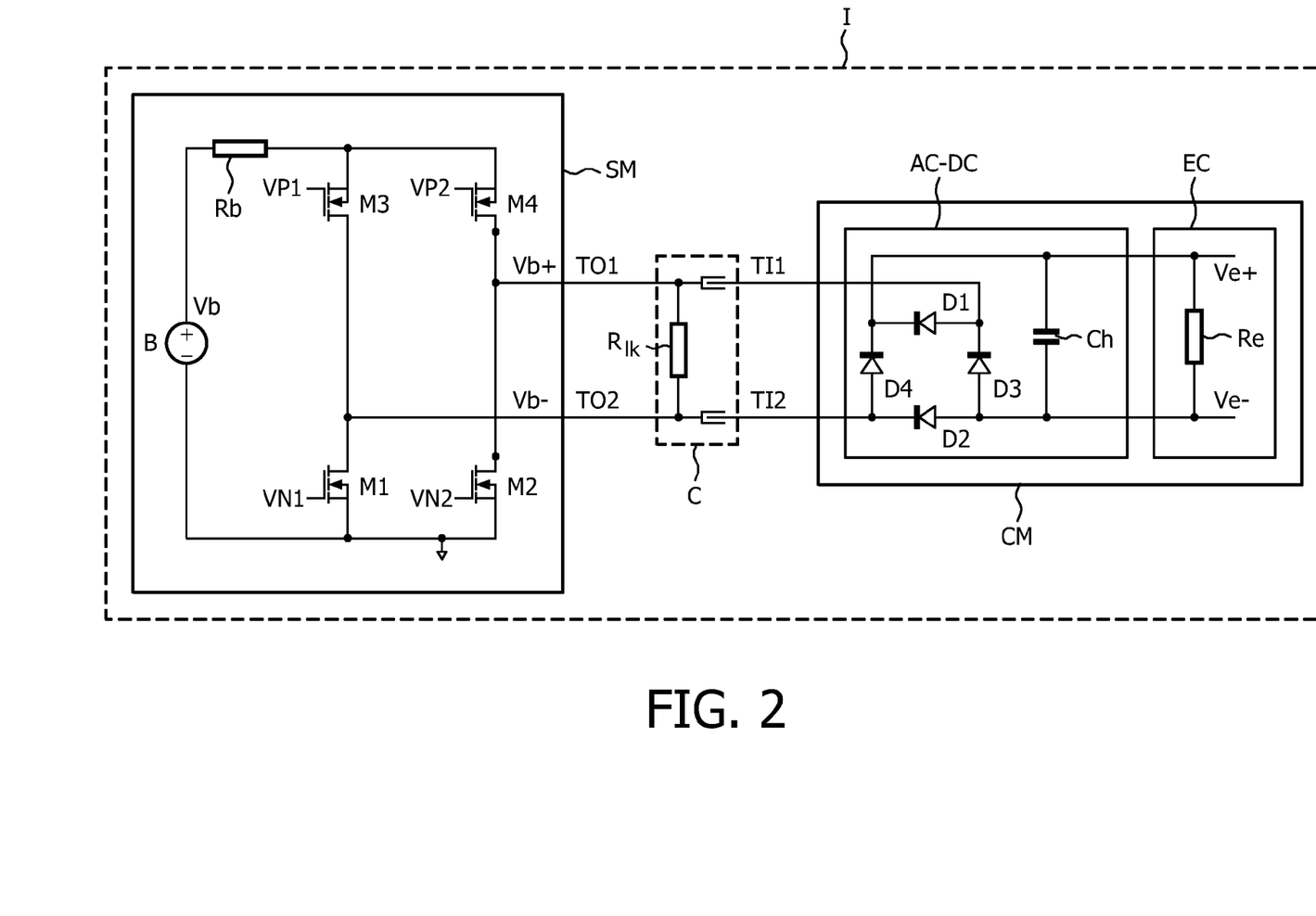
FIG. 2 shows a variation of the circuit diagram of FIG. 1, in which a leakage resistance is additionally considered.

The connector C is typically not perfectly sealed and will hence allow the entrance of (conductive) moisture leading to a leakage current between the terminals. This is represented in FIG. 2 by a leakage resistance $R_{lk}$.

If the chopped battery voltage (Vb+, Vb−) is symmetrical (i.e. 50% duty-cycle), its DC component is zero. If in addition the chop frequency $f_{chop}=1/T_{chop}$ is made sufficiently high (tens of Hz to kHz), electrolysis at the connector terminals, when moisture has entered the connector, is prevented.

The already mentioned consumer module CM comprises an AC-DC converter with a bridge comprising four diodes D1-D4 and a hold capacitor $C_h$. The diode bridge rectifies the AC voltage provided by the power input terminals TI1, TI2. The hold capacitor $C_h$ can be made small because it has only to supply energy to the electronics during the switching transients when the (synchronous) rectifier does not deliver any power. Thus almost no precious implant volume needs to be sacrificed.

The DC output voltage of the diode rectifier D1-D4 is further provided to power-consuming electronic circuits EC in which the proper functionality of the implant is realized (e.g. the scheduled delivery of stimulation pulses to neural tissue). The dissipated power of the electronic circuits EC of the implant's electronics is modeled by a resistor Re with a voltage (Ve+,Ve−) across it.

The voltage drop across the diode bridge D1-D4 becomes significant for low battery voltages Vb. In this case a (full wave) synchronous rectifier, which has a much smaller voltage drop, can be applied to improve the overall power efficiency. Such a rectifier can substantially be described as comprising an additional transistor in parallel with each diode which is switched on when current starts flowing through the diode (cf. M. I. Mihaiu: "Toward the 'Ideal Diode' using power MOSFET in full wave synchronous rectifiers for low voltage power supplies", SPEEDAM 2008, International Symposium on Power Electronics, Electrical Drives, Automation and Motion).

When a biological fluid (a saline solution) enters the connector C, (alternating) leakage currents start to flow between the connector terminals, represented by the leakage resistance $R_{lk}$ in FIG. 2. This is an extra load for the battery B, and therefore, the efficiency of the power transfer deteriorates.

The aforementioned effects can be minimized by proper mechanical design of the connector (hydrophobic materials, non-conducting bio-compatible fillers and allowing moisture in narrow short cuts only) to increase the value of the leakage resistance $R_{lk}$.

In another approach, leakage losses are reduced electronically by duty-cycling the power transfer. This will be described in the following with reference to FIG. 5, which illustrates a typical output voltage appearing at one power output terminal TO1 of the circuit of FIG. 2 in a "pulsed operating mode" of the generator G. Said output voltage comprises a train of rectangular pulses that are repeated with a frequency $1/T_{chop}$. The train of pulses is provided during a charging phase $T_{Ch}$, which is followed by a phase of inactivity in which the full-bridge power stage is not switching (for example, the power stage could be set in a state in which the power output terminals TO1, TO2 are not connected to either the battery B or ground (i.e. all transistors are not conducting), the output terminals TO1, TO2 are both connected to ground or both connected to the battery B). After the duration of one power transfer cycle, $T_p$, a new train of charging pulses follows.

Figure 5:
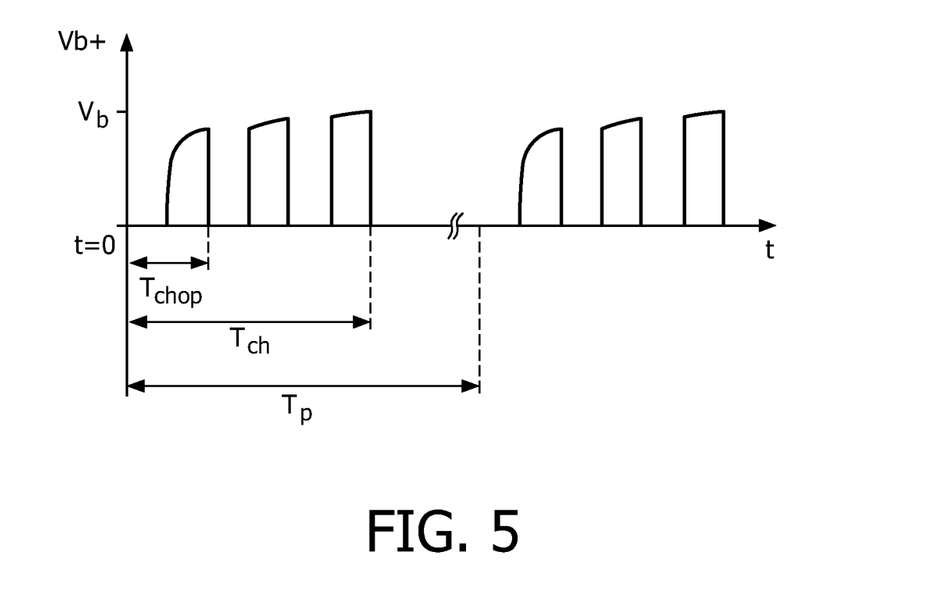
FIG. 5 illustrates the output voltage of the DC-AC converter of FIG. 1 in a pulsed operation mode.

It should be noted that the pulses of each charging period in FIG. 5 are shown with an exponential increase. This is because during the charging period, the charging current of the hold capacitor varies exponentially with time and every time output terminal TO1 is connected to the battery (i.e. transistor M4 conducts), this exponentially decaying current leads to an exponentially varying voltage across the battery B's internal resistance $R_b$ and the output resistance of transistor M4. Consequently, the pulses show an exponential increase towards the battery voltage $V_b$.

Moreover, it should be noted that the origin of the coordinate system in FIG. 5 corresponds with that indicated in FIG. 4 (because VP2 and VN2 are "high" immediately after t=0, the Vb+ terminal in FIG. 5 starts "low"/grounded).

The hold capacitor $C_h$ in the consumer module CM can very quickly be charged with a small time constant $\tau_{Ch}$, while the hold capacitor is discharged by the electronics EC with a much larger time constant $\tau_e$ ($R_e C_h$). Thus the chopping period $T_{chop}$ can be taken to be a few charging time constants $\tau_{Ch}$, and after a few chopping periods, during a time $T_{Ch} \geq T_{chop}$, the hold capacitor $C_h$ will be fully charged (because this will take approximately 5 charging time constants).

Note that the chopping period $T_{chop}$ can also be taken smaller than a single time constant $\tau_{Ch}$ (which can happen for a high chopping frequency), in which case the hold capacitor $C_h$ is only slightly charged during each chopping period. Nevertheless, if the active charging time $T_{Ch}$ is taken sufficiently long i.e. a sufficient number of time constants $\tau_{Ch}$, the hold capacitor will still be fully charged. Thus the chopping period can be chosen independently from the time constant $\tau_{Ch}$.

For the remaining phase of inactivity of the power transfer period $T_p$, all switches M1-M4 of the full-bridge DC-AC converter can be left open or the battery output terminals can be grounded (via M1 and M2). It should be noted that if the terminals are grounded, no current will flow through the diode rectifier; however, if another type of rectifier is applied, precautions must be taken to prevent short-circuiting the hold capacitor.

Thus the power transfer period $T_p$ should preferably be taken much larger than the active charging time $T_{Ch}$ (often a few chopping periods $T_{chop}$ of each a few charging time constants $\tau_{ch}$) but also much smaller than the discharge time constant $\tau_e$, i.e. $T_{Ch} \ll T_p \ll \tau_e$.

Otherwise the gain in efficiency will be lost again due to the voltage ripple on the hold capacitor $C_h$, which is also apparent from the efficiency $\eta$ of the power transfer according to ($R_{leak} = R_{lk}$)

$$\eta \approx \frac{1 - \frac{T_p}{2\tau_e}}{1 + \frac{R_e}{R_{leak}} \frac{T_{Ch}}{T_p}}$$

where $T_{Ch}/T_p$ is the charging duty-cycle. An ideal rectifier is assumed, i.e. zero voltage drop.

If one would only be interested in preventing electrolysis and would not apply any duty-cycling (e.g. to reduce the effect of leakage current), the chopping frequency is typically in the range between tens of Hz to a few kHz. However, when duty-cycling is applied, the hold capacitor will be the sole energy source for the "consumer module" once the chopping stops. When we would keep the chopping frequency low (e.g. 100 Hz, as without duty-cycling) and also would like to comply with $T_{Ch} \ll T_p$ (to reduce the effect of leakage current on the efficiency), one might end up with a quite large hold capacitor $C_h$.

To avoid this, one could for example decrease the power transfer time $T_p$ to about 100 µs, choose the active charging time $T_{ch}$ to be 10 µs (assuming this is sufficient to recharge the hold capacitor completely), and take a chopping frequency of e.g. 200 kHz (resulting in two chopping periods in the active charging time). One could then reduce the hold capacitor value and size because it is recharged more frequently.

Figure 3:
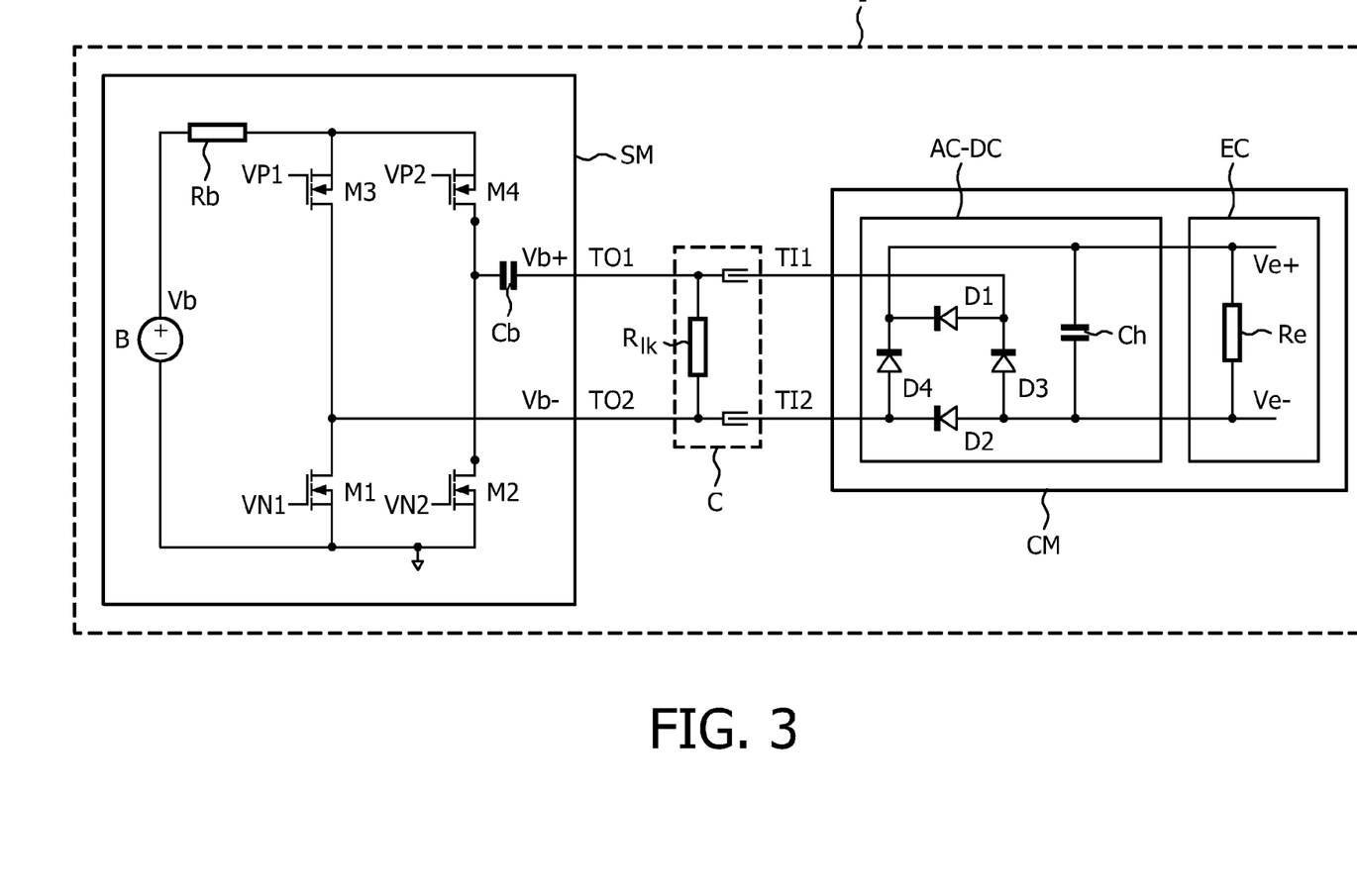
FIG. 3 shows a variation of the circuit diagram of FIG. 2, in which a blocking capacitor is additionally present.

If the electronics fails, it might happen that the DC battery voltage appears at the connector's terminals and electrolytic reactions start. This failure mode can be mitigated by insertion of a blocking capacitor $C_b$ in one of the output leads of the chopped battery voltage as shown in FIG. 3. Without duty-cycling i.e. without pulsed power transfer the conversion ratio M between battery voltage Vb and (average) supply voltage Ve for the electronics is in this case given by $$M = \frac{V_e}{V_b} = \frac{1}{1 + \frac{1}{4} \frac{C_h}{C_b} \frac{T_{chop}}{\tau_{be}}}$$

where the discharge rate across the electronics is now given by $\tau_{be}$ ($R_e[C_h \| C_b]$). The highest output voltage is achieved without hold capacitor $C_h$, because charging this capacitor costs energy and this translates into a lower supply voltage for the electronics.

The efficiency of the converter for an ideal rectifier can be calculated from $$\eta \approx \frac{V_e}{V_b}\left[1-\left(\frac{T_{chop}}{4\tau_{be}}\right)^2\right]$$

which shows that without hold capacitor, the highest efficiency is achieved. Thus the blocking capacitor effectively replaces the hold capacitor. It should be noted that a small hold capacitor is still needed to supply the electronics during the switching transients.

Duty-cycling can be applied to reduce the effect of leakage currents again, although the circuit behaves differently when a blocking capacitor is inserted. For example, all transistors of the full-bridge power stage should be made non-conducting (i.e. all transistor switches are "open") after the chopping period $T_{Ch}$ for the remainder of the power transfer period $T_p$ to prevent current flow in the connector. Although grounding the outputs of the full-bridge power stage (i.e. switching on M1 and M2 and switching off M3 and M4) can be applied when no blocking capacitor is present (as in the circuit of FIG. 2), grounding would lead to a flow of a (discharge) current in the connector when a blocking capacitor were present (as in the circuit of FIG. 3). Thus the blocking capacitor cannot act as hold capacitor in the pulsed power mode and the hold capacitor takes over this role again.

The invention can favorably be applied in an implant, for example a deep brain stimulator, in which moisture should be allowed to enter (almost unavoidable during surgery) and a safe connection (i.e. no risk of electrolysis) has to be made between battery and electronics (both hermetically sealed) to make the battery replaceable. Moreover, it can be applied in many other situations and apparatuses in which similar conditions and requirements prevail, particularly products that are used in a humid environment (e.g. outdoor environment, bathroom, swimming pool etc.).

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An electronic apparatus, comprising:
    a supply module with a DC power source and power output terminals;
    a consumer module with power input terminals and power-consuming electronic circuits; and
    a connector for reversibly connecting corresponding power output terminals and power input terminals,
    wherein the supply module includes a DC-AC converter that is arranged between the DC power source and the power output terminals to convert DC power from the DC power source to AC power and to pulse the AC power for delivering pulsed AC power to the power output terminals that are reversibly connected to the power input terminals,
    wherein the pulsed AC power includes a train of pulses including at least two consecutive pulses having positive amplitudes, the at least two consecutive pulses including a first pulse followed by a second pulse, and
    wherein a maximum amplitude of the second pulse is greater than a maximum amplitude of the first pulse.

2. The apparatus according to claim 1, wherein the DC power source is a battery and the supply module including the battery and the DC-AC converter is replaceable for providing a desired and safe power transfer to the consumer module via the connector.

3. The apparatus according to claim 1, wherein the supply module and/or the consumer module is hermetically sealed with the exception of the associated power output terminals or power input terminals, respectively.

4. The apparatus according to claim 1, wherein a blocking capacitor is arranged between the DC-AC converter and one power output terminal.

5. The apparatus according to claim 1, wherein a frequency of an AC voltage of the AC power converted by the DC-AC converter ranges between 1 Hz and 1 MHz.

6. The apparatus according to claim 1, wherein the DC-AC converter includes transistors configured to convert the DC power to the AC power, and wherein all the transistors are turned off during a predetermined time for pulsing the AC power and providing the pulsed AC power.

7. The apparatus according to claim 1, wherein the train of pulses are provided during periods of activity, and wherein the periods of activity are long enough to substantially charge an intermediate power storage in the consumer module.

8. The apparatus of claim 7, wherein the periods of activity are separated periods of inactivity.

9. The apparatus according to claim 1, wherein the connector comprises hydrophobic materials, redundant contacts, and/or substantially no voids in its connected state.

10. The apparatus according to claim 1, wherein the apparatus is an implantable device including a Deep Brain Stimulation system, a surgical tool, or an ingestible electronic product.

11. The apparatus according to claim 1, wherein the apparatus is a product of consumer electronics including a media player or recorder, a cell phone, a calculator, equipment for pipelines, a shaver, a measuring device, equipment used by divers, or a tool.

12. The apparatus according to claim 1, further comprising an AC DC converter that is arranged between the power input terminals and the power-consuming electronic circuits.

13. The apparatus according to claim 12, further comprising a hold capacitor that connects the outputs of the AC DC converter.

14. The apparatus of claim 13, wherein a charging time constant of the hold capacitor $\tau_{ch}$ is smaller than a discharging time constant of the hold capacitor $\tau_e$, wherein the train of pulses is provided during active charging time $T_{ch}$ followed by an inactivity period devoid of pulses, the active charging time $T_{ch}$ and the inactivity period defining a power transfer period $T_p$, and wherein $T_{ch} \ll T_p \ll \tau_e$.

15. The apparatus of claim 13, wherein the hold capacitor provides power during periods in between the pulsed AC power for delivering continuous power to the power-consuming electronic circuits.

16. The apparatus of claim 13, wherein a period of pulses of the train of pulses is chosen independently from a time constant of the hold capacitor.

17. A method for transferring electrical power from a supply module with a DC power source and power output terminals to a consumer module with power input terminals and a power-consuming electronic circuit via a connector for reversibly connecting corresponding power output terminals and power input terminals,
    said method comprising acts of:
        converting DC voltage provided by the DC power source into an AC voltage with a DC-AC converter;
        pulsing the AC voltage to provide a train of pulses including at least two consecutive pulses having positive amplitudes, the at least two consecutive pulses including a first use followed by a second pulse, wherein a maximum amplitude of the second pulse is greater than a maximum amplitude of the first pulse; and providing the pulsed AC voltage to the power output terminals.

18. The method of claim 17, wherein the converting act is performed by selectively operating transistors, and wherein the pulsing act is performed by turning off all the transistors during a predetermined time.

19. The method of claim 17, wherein the train of pulses is provided during periods of activity, and wherein the periods of activity are long enough to substantially charge an intermediate power storage in the consumer module.

20. The method of claim 17, further comprising acts:
connecting a hold capacitor between outputs of the power-consuming electronic circuit; and
choosing a period of pulses of the train of pulses independently from a time constant of the hold capacitor.

21. A supply module for providing pulsed AC power, comprising:
a DC power source;
power output terminal; and
a DC-AC converter that is arranged between the DC power source and the power output terminals to convert DC power from the DC power source to AC power and to pulse the AC power for delivering pulsed AC power to the power input terminals,
wherein the pulsed AC power includes a train of pulses including at least two consecutive pulses having positive amplitudes, the at least two consecutive pulses including a first pulse followed by a second pulse, and
wherein a maximum amplitude of the second pulse is greater than a maximum amplitude of the first pulse.

* * * * *